United States Patent

Inoue

(10) Patent No.: US 9,928,865 B2
(45) Date of Patent: Mar. 27, 2018

(54) FLUOROPOLYETHER COMPOUND, AND LUBRICANT AND MAGNETIC DISC USING SAME

(71) Applicant: MORESCO CORPORATION, Kobe-shi, Hyogo (JP)

(72) Inventor: Aya Inoue, Kobe (JP)

(73) Assignee: MORESCO CORPORATION, Kobe-shi (JP)

( * ) Notice: Subject to any disclaimer, the term of this patent is extended or adjusted under 35 U.S.C. 154(b) by 291 days.

(21) Appl. No.: 14/764,339

(22) PCT Filed: Sep. 17, 2014

(86) PCT No.: PCT/JP2014/075334
§ 371 (c)(1),
(2) Date: Jul. 29, 2015

(87) PCT Pub. No.: WO2015/087596
PCT Pub. Date: Jun. 18, 2015

(65) Prior Publication Data
US 2015/0371671 A1   Dec. 24, 2015

(30) Foreign Application Priority Data

Dec. 9, 2013  (JP) .................................. 2013-254113

(51) Int. Cl.
G11B 5/66       (2006.01)
G11B 5/725      (2006.01)
(Continued)

(52) U.S. Cl.
CPC .............. *G11B 5/725* (2013.01); *C07F 9/659* (2013.01); *C07F 9/65815* (2013.01); (Continued)

(58) Field of Classification Search
CPC ..... G11B 5/75; C07F 9/65815; C08G 65/007; C10M 2217/003; C10M 2225/003
See application file for complete search history.

(56) References Cited

U.S. PATENT DOCUMENTS

2002/0183211 A1   12/2002   Akada et al.
2008/0020171 A1   1/2008    Wakabayashi et al.
(Continued)

FOREIGN PATENT DOCUMENTS

JP   2008-59683 A   3/2008
JP   4137447 B2     8/2008
(Continued)

OTHER PUBLICATIONS

Kasai, "Perfluoropolyethers: Intramolecular Disproportionation" Macromolecules, 1992, vol. 25, pp. 6791-6799.
(Continued)

*Primary Examiner* — Holly Rickman
(74) *Attorney, Agent, or Firm* — Westerman, Hattori, Daniels & Adrian, LLP

(57) ABSTRACT

A compound of the formula (1), and lubricant, and magnetic disk each using the same $$A-O-CH_2-Rf-CH_2-B \quad (1)$$

wherein A is a group of the formula (a) below, B is a group of the formula (b) or (c) or (d) below, p is 0, 1 or 2, q is a real number of 2 to 10, R is $C_{1-4}$ fluoroalkyl, Ar is unsubstituted or substituted aromatic group with $C_{1-30}$ alkyl or $C_{1-30}$ alkoxyl, Rf is $-CF_2CF_2O(CF_2CF_2CF_2O)_xCF_2CF_2-$ or $-CF_2CF_2CF_2O(CF_2CF_2CF_2CF_2O)_yCF_2CF_2CF_2-$, x and y are each a real number of 0 to 50.

(Continued)

US 9,928,865 B2
Page 2

(a)

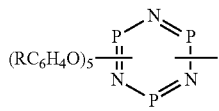

(b)

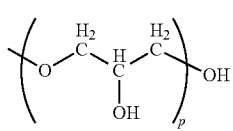

(c)

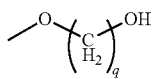

(d)

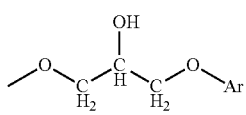

8 Claims, 1 Drawing Sheet

(51) Int. Cl.
*C07F 9/6593* (2006.01)
*C10M 105/74* (2006.01)
*C07F 9/659* (2006.01)

(52) U.S. Cl.
CPC .... *C10M 105/74* (2013.01); *C10M 2223/083* (2013.01); *C10M 2225/003* (2013.01); *C10N 2240/204* (2013.01)

(56) References Cited

U.S. PATENT DOCUMENTS

| | | | | |
|---|---|---|---|---|
| 2009/0291325 | A1* | 11/2009 | Xu | C07F 9/65815 428/800 |
| 2010/0136371 | A1 | 6/2010 | Shimizu et al. | |
| 2011/0143165 | A1* | 6/2011 | Kobayashi | C08G 65/007 428/800 |
| 2013/0034749 | A1 | 2/2013 | Shimizu et al. | |
| 2013/0288080 | A1* | 10/2013 | Yan | C07F 9/65815 428/833 |

FOREIGN PATENT DOCUMENTS

| | | |
|---|---|---|
| JP | 4570622 B2 | 10/2010 |
| JP | 5358837 B2 | 12/2013 |
| WO | 01/21630 A1 | 3/2001 |
| WO | 2006/009057 A1 | 1/2006 |
| WO | 2008/140121 A1 | 11/2008 |
| WO | 2011/136379 A1 | 11/2011 |

OTHER PUBLICATIONS

International Search Report dated Dec. 9, 2014, issued in counterpart Application No. PCT/JP2014/075334 (2 pages).

\* cited by examiner

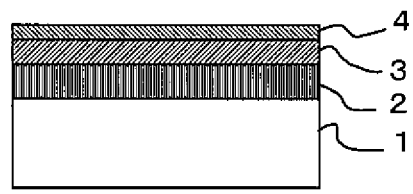

FLUOROPOLYETHER COMPOUND, AND LUBRICANT AND MAGNETIC DISC USING SAME

TECHNICAL FIELD

The present invention relates to fluoropolyether compounds having a cyclophosphazene group and hydroxyl group, lubricants containing the compound and magnetic disks having the lubricant applied thereto.

BACKGROUND ART

With an increase in the recording density of magnetic disks, the distance between the magnetic disk serving as a recording medium and the head for use in recording of information or playback has become almost nil close to contact therebetween. The magnetic disk is provided over the surface thereof with a carbon protective film or lubricant film for the purpose of diminishing abrasion due to the contact or sliding of the head thereon or preventing contamination of the disk surface.

The carbon protective film is produced generally by the sputtering process or CVD process. Since the disk surface is protected with the two films, i.e., the carbon protective film and the lubricant film thereover, the interaction between the carbon protective film and the lubricant is important.

The lubricants generally in use are perfluoropolyethers having functional groups. Examples of functional groups are hydroxyl, amino and cyclophosphazene group. More specific examples of lubricants having hydroxyl include Fomblin Ztetraol manufactured by Solvay Solexis Inc., PHOSFAROL A20H, PHOSFAROL ADOH, PHOSFAROL A20H-DD, each product of MRESCO Corporation. As mentioned later, these four lubricants are low in resistance to Lewis acids. These are decomposed by Lewis acids and are concerned to accompany a great weight reduction by heat. They are to be improved in decomposition resistance.

PHOSFAROL A20H is a fluoropolyether having both hydroxyl and cyclophosphazene groups (Patent Literature 1). PHOSFAROL ADOH is a cyclophosphazene to which is bonded one perfluoroether chain having two hydroxyl groups (Patent Literature 2). PHOSFAROL A20H-DD is a cyclophosphazene to which are bonded two perfluoroether chains having two hydroxyl groups (Patent Literature 3).

Fomblin Ztetraol exhibits good properties to adhere to the disk due to the presence of the hydroxyl at opposite terminals of the molecule, does not spatter even when the disk rotates at a high speed and is capable of retaining the form of a lubricant film. However, this perfluoropolyether compound is low in resistance to Lewis acids, reacts with $Al_2O_3$ in the component of the head and becomes cleaved in its main chain (see, for example, Nonpatent Literature 1). When this cleavage progresses, the compound becomes lower in molecular weight, eventually vaporizing off from the magnetic disk surface and failing to retain the form of a lubricant film in systems involving contact or sliding movement between the head and disk.

On the other hand, PHOSFAROL A20H, PHOSFAROL ADOH or PHOSFAROL A20H-DD has at one terminal of the molecule a hydroxyl group contributing to the adhesion to the disk and at the other terminal a cyclophosphazene group for inhibiting the cleavage of the perfluoropolyether main chain with Lewis acids. Accordingly, the lubricant does not spatter even if the disk is in high-speed rotation, the compound is inhibited from decomposing with the $Al_2O_3$ in the component of the head and the lubricant is capable of retaining the film form. However, these PHOSFAROLs, similar to Fomblin Ztetraol, have a main chain which is low in resistance to Lewis acids, and are insufficient to restrict cleavage of its main chain due to the presence of a cyclophosphazene group, and react with $Al_2O_3$ in the component of the head and becomes cleaved in its main chain. When this cleavage progresses, the compound becomes lower in molecular weight, eventually vaporizing off from the magnetic disk surface and failing to retain the form of a lubricant film in systems involving contact or sliding movement between the head and disk.

[Patent Literature 1] Jap. Patent No. 4137447
[Patent Literature 2] Jap. Patent No. 4570622
[Patent Literature 1] WO 2008/140121
[Nonpatent Literature 1] Macromolecules, 1992, Vol. 25, pp. 6791-6799

An object of the present invention is to provide a stable compound which remains free of decomposition even when brought into contact with the magnetic head, a lubricant using the compound and magnetic disk having the lubricant applied thereto.

DISCLOSURE OF THE INVENTION

The present invention provides the following invention.
1. A compound of the formula (1)

wherein A is a group of the formula (a) below, B is a group of the formula (b) or (c) or (d) below, p is 0, 1 or 2, q is a real number of 2 to 10, R is $C_{1-4}$ fluoroalkyl, Ar is unsubstituted or substituted aromatic group with $C_{1-30}$ alkyl or $C_{1-30}$ alkoxyl, Rf is $—CF_2CF_2O(CF_2CF_2CF_2O)_xCF_2CF_2—$ or $—CF_2CF_2CF_2O(CF_2CF_2CF_2CF_2O)_yCF_2CF_2CF_2—$, x and y are each a real number of 0 to 50.

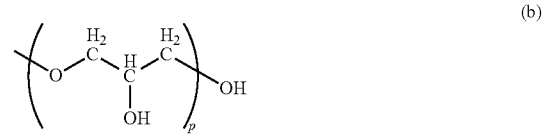

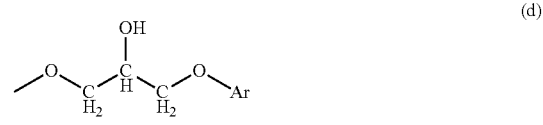

2. A compound as defined in (1) above wherein B is (b), and p is 1 or 2.
3. A lubricant containing a compound of the formula (1).
4. A lubricant containing a compound of the above (2).
5. A magnetic disk having at least a recording layer and a protective layer formed over a substrate, and a lubricant layer provided over a surface of the resulting assembly and comprising a compound containing a perfluoropolyether structure, the disk having a compound of the formula (1) as the lubricant layer.

6. A magnetic disk as defined in (5) above which has a compound of the above (2) as the lubricant layer.

[1] The fluoropolyether of the formula (1) of the invention is a fluoropolyether compound having a cyclophosphazene group at one terminal and hydroxyl group(s) or an aromatic group at the other terminal.

[1-1] Preparation Process 1

The compound of the formula (1) which has a cyclophosphazene group at one terminal and a group of the formula (b) at the other terminal is prepared, for example, by the following process. Cyclophospazene having five $RC_4H_4O-$ groups and one chlorine atoms and a fluoropolyether having the formula of $HOCH_2-Rf-CH_2-$ (b) are heated along with metallic sodium with stirring. The reaction is conducted at a temperature of 50 to 100° C., preferably 60 to 80° C. for 10 to 70 hours, preferably for 20 to 50 hours. It is desirable to use 0.5 to 3 equivalents of the fluoropolyether and 1 to 4 equivalents of metallic sodium, based on the cyclophosphazene. The reaction mixture was thereafter treated, for example, by washing with water and column chromatography for purification to obtain the desired fluoropolyether compound having a cyclophosphazene group at one terminal and a group of the formula (b) at the other terminal.

The R in the substituent of the cyclophosphazene is a $C_{1-4}$ fluoroalkyl group, such as 1,1,2,2-tetrafluoroethyl group, 1,1,2,2,3,3-hexafluoropropyl group and 1,1,2,2,3,3,4,4-octafluorobutyl group. The substitution position of R may be any of the ortho position, meta position and para position.

Examples of fluoropolyethers having the formula of $HOCH_2-Rf-CH_2-$ (b) are
$HOCH_2CF_2CF_2O(CF_2CF_2CF_2O)_xCF_2CF_2CH_2OH$,
$HOCH_2CF_2CF_2CF_2O(CF_2CF_2CF_2CF_2O)_yCF_2$
$CF_2CF_2CH_2H$, $HOCH_2CF_2CF_2O(CF_2CF_2CF_2O)_xCF_2CF_2CH_2OCH_2CH(OH)CH_2OH$,
$HOCH_2CF_2CF_2CF_2CF_2O(CF_2CF_2CF_2CF_2O)_yCF_2$
$CF_2CF_2CH_2OCH_2CH(OH)CH_2OH$, $HOCH_2CF_2CF_2O$
$(CF_2CF_2CF_2O)_xCF_2CF_2CH_2OCH_2OH(OH)CH_2OCH_2CH$
$(OH)CH_2OH$ and $HOCH_2CF_2CF_2CF_2O$
$(CF_2CF_2CF_2CF_2CF_2O)_yCF_2CF_2CF_2CH_2OCH_2CH(OH)$
$CH_2OCH_2CH(OH)CH_2OH$, wherein x and y are each a real number of 0 to 50, preferably 0 to 30, more preferably 0 to 20. These compounds have a molecular weight distribution. In the group (b), p is 0, 1 or 2, preferably p is 1 or 2, particularly preferably p is 1.

[1-2] Preparation Process 2

The compound of the formula (1) which has a cyclophosphazene group at one terminal and a group of the formula (c) at the other terminal is prepared in the similar manner to the preparation process 1 except that a fluoropolyether having the formula of $HOCH_2-Rf-CH_2-$ (c) is used in place of the fluoropolyether having the formula of $HOCH_2-Rf-CH_2-$ (b).

Examples of fluoropolyethers having the formula of $HOCH_2-Rf-CH_2-$ (c) are $HOCH_2CF_2CF_2O$
$(CF_2CF_2CF_2O)_xCF_2CF_2CF_2CH_2O(CH_2)qOH$ and
$HOCH_2CF_2CF_2CF_2CF_2O(CF_2CF_2CF_2CF_2O)_yCF_2CF_2$
$CF_2CF_2CH_2O(CH_2)qOH$, wherein x and y are the same as above, q is a real number of 2 to 10, preferably 2 to 6, more preferably 2 to 4. These compounds have a molecular weight distribution.

[1-3] Preparation Process 3

The compound of the formula (1) which has a cyclophosphazene group at one terminal and a group of the formula (d) at the other terminal is prepared in the similar manner to the preparation process 1 except that a fluoropolyether having the formula of $HOCH_2-Rf-CH_2-$ (d) is used in place of the fluoropolyether having the formula of $HOCH_2-Rf-CH_2-$ (b).

Examples of fluoropolyethers having the formula of $HOCH_2-Rf-CH_2-$(d) are $HOCH_2CF_2CF_2O$
$(CF_2CF_2CF_2O)_xCF_2CF_2CH_2OCH_2CH(OH)CH_2OAr$ and
$HOCH_2CF_2CF_2CF_2O(CF_2CF_2CF_2CF_2O)_xCF_2CF_2$
$CF_2CH_2OCH_2CH(OH)CH_2OAr$, wherein x and y are the same as above, Ar is unsubstituted or substituted aromatic group with $C_{1-30}$ alkyl or $C_{1-30}$ alkoxyl. Examples of aromatic groups are phenyl and naphthyl. Examples of $C_{1-30}$ alkyl groups are methyl, ethyl, propyl, butyl, octyl, tetradecyl, octadecyl, eicosanyl, pentacosanyl, heptacosanyl and triacontyl. Examples of $C_{1-30}$ alkoxyl groups are those corresponding to the above alkyl groups. The substitution position of alkyl or alkoxyl group may be any of the ortho position, meta position, para position or all positions of the aromatic group.

[1-4] Method of Use

The compound of the present invention is applied to the magnetic disk surface by diluting the compound with a solvent and coating the disk surface with the diluted compound. Examples of useful solvents are PF-5060, PF-5080, HFE-7100 and HFE-7200 manufactured by 3M, Vertrel-XF, product of DuPont, etc. The concentration of the compound as diluted is up to 1 wt. %, preferably 0.001 to 0.1 wt. %.

While the compound of the invention is usable singly, the compound can be used also as mixed in a desired ratio with another material, such as Fomblin Zdol, Ztetraol, Zdol TX, AM manufactured by Solvay Solexis, Demnum manufactured by Daikin Industries, Ltd., Krytox manufactured by DuPont, or the like.

[1-5] Use

The compound of the present invention is useful, for example, as a lubricant for giving improved sliding characteristics to the magnetic disk in magnetic disk devices. The compound of the invention is characterized by the formation of hydrogen bonding of hydroxyl with a polar site, the covalent bond thereof with a dangling bond (unlinked bond) and further by the interaction of the cyclophosphazene group with a carbon unsaturated bond. Accordingly, the compound is usable as a surface protective film for photomagnetic recording devices, magnetic tapes, plastics and like organic materials having a carbon protective film, and also as a surface protective film for inorganic materials such as glass and metal.

(2) Concerning Magnetic Disks

[2-1] Structure of Magnetic Disks

FIG. 1 shows a sectional view schematically showing the magnetic disk of the invention.

The magnetic disk of the invention comprises a substrate 1, at least one recording layer 2 formed on the substrate 1, a protective layer 3 on the recording layer 2 and a lubricant layer 4 formed thereon, as an outermost layer, which contains the compound of the invention.

The substrate 1 is composed of aluminum alloy, glass and like ceramics, polycarbonate or the like.

The recording layer of the magnetic disk, i.e., the magnetic layer is composed of mainly elements capable of forming ferromagnetic bodies, such as iron, cobalt or nickel, alloy or oxide containing chromium, platinum or tantalum in addition to such elements. These materials are applied by, e.g., a plating method or a sputtering method.

The protective layer is formed of carbon, SiC, $SiO_2$ or the like. The layer is formed by a sputtering method or CVD method.

[2-2] Method of Forming Lubricant Layer

Lubricant layers presently used are up to 30 Å in thickness, so that when a lubricant having a viscosity of higher than about 100 mPa·s at 20° C. is applied as it is, the resulting film is likely to have an excessively large thickness. Accordingly the lubricant for use in coating is used as dissolved in a solvent. When the compound of the present invention is applied as dissolved in a solvent, the film thickness to be obtained is easy to control in the case where the present compound serves singly as a lubricant and also in the case where the compound is used as mixed, for example, with Fomblin Zdol, Ztetraol, Zdol TX, AM, products of Solvay Solexis, Demnum manufactured by Daikin Industries, Ltd., Krytox manufactured by Dupont, etc. The concentration varies with the method and conditions of application, mixing ratio, etc. The lubricant film of the present invention is preferably 5 to 15 Å in thickness.

In order to assure the lubricant of improved adhesion to the ground layer, the lubricant applied can be subjected to heat treatment or ultraviolet treatment. The heat treatment is conducted at 60 to 150° C., preferably at 80 to 150° C. The ultraviolet treatment is conducted using ultraviolet rays of 185 nm and 254 nm in main wavelength.

[2-3] Application

The magnetic disk of the invention can be applied to a magnetic disk apparatus which can accommodate the disk and which is provided with a magnetic disk drive including a head for recording, reproducing and erasing information and a motor for rotating the disk; and with a control system for controlling the drive.

The magnetic disk of the invention and the magnetic disk apparatus produced using the magnetic disk thereof can be applied for the following: electronic computers, and outer memories for word processors; and can be also applied in navigation systems, games, cellular phone, PHS (personal handyphone system) and like instruments and machines and inner and outer memories for prevention of crimes in buildings, and for management/control systems of power plants.

BRIEF DESCRIPTION OF THE DRAWING

FIG. 1 is a section view showing the structure of the magnetic disk of the invention.

BEST MODE FOR CARRYING OUT THE INVENTION

The invention will be described in more detail with reference to the following examples and test examples to which, however, the invention is not limited. $^{19}$F-NMR (solvent: none, reference material: OCF$_2$C$\underline{F}_2$CF$_2$O in the obtained product being taken as −129.7 ppm): $^1$H-NMR (solvent: perfluorobenzene, reference material: D$_2$O)

Example 1

Preparation of A-O—CH$_2$—Rf—CH$_2$—B (Compound I)

A is a group of the formula (a) below, B is a group of the formula (b) below, p is 1, R is m-CF$_3$, and Rf is —CF$_2$CF$_2$O—(CF$_2$CF$_2$CF$_2$O)$_x$CF$_2$CF$_2$—.

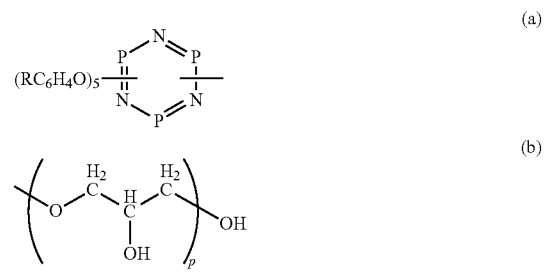

In an argon atmosphere, ditrifluoromethylbenzene (114 g), penta-(trifluoromethylphenoxy)-cyclotriphosphonitrile chloride (114 g), HOCH$_2$CF$_2$CF$_2$O(CF$_2$CF$_2$CF$_2$O)$_x$CF$_2$CF$_2$CF$_2$OCH$_2$CH$_2$(OH)CH$_2$OH (2000 in average molecular weight) which corresponds to the formula of HOCH$_2$—Rf—CH$_2$-(b) and metallic sodium (0.9 g) were mixed and stirred at 70° C. for 19 hours. The resulting mixture was washed with water and subsequently purified by column chromatography, affording 46 g of the desired Compound I.

Compound I was a colorless transparent liquid and had a density of 1.75 g/cm$^3$ at 20° C. Compound I was identified by NMR with the result shown. Compound I as obtained was used for $^{19}$F-NMR. $^1$H-NMR analysis was conducted by a sample obtained by adding trifluoroacetic anhydride to Compound I to modify the hydroxyl to an ester.

$^{19}$F-NMR (solvent: none):

δ=−64.6 ppm

[15F, [P$_3$N$_3$ (OC$_6$H$_4$C$\underline{F}_3$)$_5$]—OCH$_2$—]

δ=−86.5 ppm, −124.2 ppm

[4F, —C$\underline{F}_2$C$\underline{F}_2$CH$_2$OCH$_2$CH(OH)CH$_2$OH]

δ=−86.1 ppm, −124.5 ppm

[4F, [P$_3$N$_3$(OC$_6$H$_4$CF$_3$)$_5$]—OCH$_2$C$\underline{F}_2$C$\underline{F}_2$—]

x=12.6

$^1$H-NMR (solvent: perfluorohexane, reference material: D$_2$O):

δ=3.92~4.01 ppm

[4H, —CF$_2$CH$_2$OC$\underline{H}_2$CH(OCOCF$_3$)C$\underline{H}_2$OCOCF$_3$],

δ=3.95~3.91 ppm

[2H, [P$_3$N$_3$ (OC$_6$H$_4$CF$_3$)$_5$]—OCH$_2$CF$_2$—],

δ=4.47~4.53 ppm

[2H, —CF$_2$C$\underline{H}_2$OCH$_2$CH(OCOCF$_3$)CH$_2$OCOCF$_3$],

δ=5.31~5.36 ppm

[1H, —CF$_2$CH$_2$OCH$_2$C$\underline{H}$(OCOCF$_3$)CH$_2$OCOCF$_3$]

Example 2

Preparation of A-O—CH$_2$—Rf—CH$_2$—B (Compound II)

Compound II was prepared in the same manner as in Example 1 except that HOCH$_2$CF$_2$CF$_2$CF$_2$O (CF$_2$CF$_2$CF$_2$CF$_2$O)$_y$CF$_2$CF$_2$CF$_2$CH$_2$OCH$_2$CH(OH) CH$_2$OH (40 g, 2000 in average molecular weight) was used as the fluoropolyether of the formula HOCH$_2$—Rf—CH$_2$—(b).

Compound II was a colorless transparent liquid and had a density of 1.75 g/cm$^3$ at 20° C. Compound II was identified by NMR with the result shown. Compound II as obtained was used for $^{19}$F-NMR.

$^{19}$F-NMR (solvent: none):
δ=−64.6 ppm
[15F, [P$_3$N$_3$(OC$_6$H$_4$C$\underline{F}_3$)$_5$]—OCH$_2$—]
δ=−120.3 ppm
[4F, —CF$_2$CF$_2$C$\underline{F}_2$CH$_2$OCH$_2$CH(OH)CH$_2$OH, [P$_3$N$_3$(OC$_6$H$_4$CF$_3$)$_5$]—OCH$_2$C$\underline{F}_2$CF$_2$CF$_2$—]
δ=−127.6 ppm
[4F, —CF$_2$C$\underline{F}_2$CF$_2$CH$_2$OCH$_2$CH(OH)CH$_2$OH, [P$_3$N$_3$(OC$_6$H$_4$CF$_3$)$_5$]—OCH$_2$CF$_2$C$\underline{F}_2$CF$_2$—]
y=7.0

Example 3

Preparation of A-O—CH$_2$—Rf—CH$_2$—B (Compound III)

Compound III was prepared in the same manner as in Example 1 except that HOCH$_2$CF$_2$CF$_2$O(CF$_2$CF$_2$CF$_2$O)$_x$CF$_2$CF$_2$CH$_2$O(CH$_2$)$_2$OH (47 g, 2000 in average molecular weight) was used as the fluoropolyether of the formula HOCH$_2$—Rf—CH$_2$— (c).

Compound III was a colorless transparent liquid and had a density of 1.74 g/cm$^3$ at 20° C. Compound III was identified by NMR with the result shown. Compound III as obtained was used for $^{19}$F-NMR.

$^{19}$F-NMR (solvent: none):
δ=−64.1 ppm
[15F, [P$_3$N$_3$(OC$_6$H$_4$C$\underline{F}_3$)$_5$]—OCH$_2$—]
δ=−86.7 ppm
[2F, —C$\underline{F}_2$CF$_2$CH$_2$O(CH$_2$)$_2$OH]
δ=−124.4 ppm
[2F, —CF$_2$C$\underline{F}_2$CH$_2$O(CH$_2$)$_2$OH]
δ=−86.3 ppm
[2F, [P$_3$N$_3$ (OC$_6$H$_4$CF$_3$)$_5$]—OCH$_2$CF$_2$C$\underline{F}_2$—]
δ=−124.8 ppm
[2F, [P$_3$N$_3$ (OC$_6$H$_4$CF$_3$)$_5$]—OCH$_2$C$\underline{F}_2$CF$_2$—]
x=9.8

Example 4

Preparation of A-O—CH$_2$—Rf—CH$_2$—B (Compound IV)

Compound IV was prepared in the same manner as in Example 1 except that HOCH$_2$CF$_2$CF$_2$O(CF$_2$CF$_2$CF$_2$O)$_x$CF$_2$CF$_2$CH$_2$OCH$_2$CH(OH)CH$_2$O— methoxyphenyl-p (40 g, 2000 in average molecular weight) was used as the fluoropolyether of the formula HOCH$_2$—Rf—CH$_2$— (d).

Compound IV was a colorless transparent liquid and had a density of 1.75 g/cm$^3$ at 20° C. Compound IV was identified by NMR with the result shown. Compound IV as obtained was used for $^{19}$F-NMR.

$^{19}$F-NMR (solvent: none):
δ=−63.8 ppm
(15F, [P$_3$N$_3$(OC$_6$H$_4$C$\underline{F}_3$)$_5$]—OCH$_2$—)
δ=−86.2 ppm, −123.9 ppm
(4F, —C$\underline{F}_2$C$\underline{F}_2$CH$_2$OCH$_2$CH(OH)CH$_2$OAr)
δ=−86.1 ppm, −124.5 ppm
(4F, [P$_3$N$_3$(OC$_6$H$_4$CF$_3$)$_5$]—OCH$_2$C$\underline{F}_2$C$\underline{F}_2$—)
x=9.4

Test Example 1

Measurement of Decomposition Resistance to Aluminum Oxide

A sample was used which was prepared from Compound I prepared in Example 1, by adding 20 wt. % of Al$_2$O$_3$ (ICN Alumina B, Akt. I, product of MP Biomedicals, 100 μm in mean particle size) to the compound, intensely shaking the mixture and thereafter thoroughly agitating the mixture with ultrasonic waves. The sample was checked for thermal behavior in the presence of Al$_2$O$_3$ using a thermal analyzer (TG/TDA). The sample (20 mg) was placed into an aluminum container and heated in a nitrogen atmosphere at a constant temperature of 250° C., and the weight reduction of the compound was measured after the lapse of 100 minutes and 200 minutes. For comparison, 20 mg of Compound I was thermally analyzed in the same manner as above with the exception of adding no Al$_2$O$_3$. For further comparison, Compounds V to XIII were also used.

Compound V: PHOSFAROL ADOH, product of MORESCO Corporation
Compound VI: PHOSFAROL A20H-2000, product of MORESCO Corporation
Compound VII: PHOSFAROL A20H-DD
Compound XIII: Fomblin Ztetraol-2000S, product of Solvay Solexis Inc.

A is a group of the formula (a) below, B is a group of the formula (b) below, p is 1, R is m-CF$_3$, and Rf is —CF$_2$CF$_2$O—(CF$_2$CF$_2$O)$_a$(CF$_2$O)$_b$CF$_2$—, a is 10.5, b is 10.1.

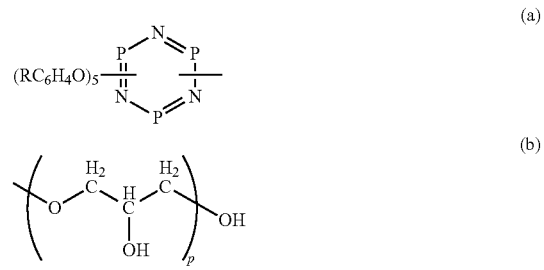

Table 1 shows the evaluation results. Table 1 reveals that the fluoropolyether compounds of the present invention are found to have high decomposition resistance compared with Compounds V to XIII.

TABLE 1

| | Ratio of decrease in weight (%) | | | |
| --- | --- | --- | --- | --- |
| | Absence of Al$_2$O$_3$ | | Presence of Al$_2$O$_3$ | |
| Specimen | After 100 min | After 200 min | After 100 min | After 200 min |
| Compound I | 1 | 1 | 3 | 3 |
| Compound V (ADOH) | 2 | 3 | 5 | 9 |
| Compound VI (A20H-2000) | 5 | 9 | 6 | 8 |
| Compound VII (A20H-DD) | 3 | 4 | 4 | 5 |
| Compound VIII (Ztetraol-2000S) | 26 | 37 | 39 | 97 |

Test Example 2

Measurement of Bonded Ratio

Compound I prepared in Example 1 was dissolved in Vertrel-XF, product of DuPont. The solution was 0.1 wt. % in the concentration of the compound. A magnetic disk, 2.5 inches in diameter, was immersed in the solution for 1 minute and then withdrawn at a rate of 2 mm/s. The disk was thereafter held in a constant-temperature chamber at 150° C. for 10 minutes to promote the adhesion of the lubricant to the disk surface. The average film thickness of the compound on the disk was subsequently measured by a Fourier Transform Infrared Spectrometer (FT-IR). This film thickness was taken as f Å. Next, the disk was immersed in Vertrel-XF for 10 minutes, withdrawn at a rate of 10 mm/s and thereafter allowed to stand at room temperature for the evaporation of the solvent. The compound remaining on the disk was thereafter checked by FT-IR for average film thickness. This film thickness was taken as b Å. The bonded ratio generally in use was used as an indicator for showing the strength of adhesion of the film to the disk. The bonded ratio was expressed by the equation given below.

Bonded ratio(%)=100×b/f

Used for comparison were Compound V [PHOSFAROL ADOH] and a perfluoropolyether having two hydroxyl groups at each of opposite terminals (Fomblin Ztetraol-2000S, product of Solvay Solexis, Compound XIII).
$HOCH_2CH(OH)CH_2OCH_2CF_2O(CF_2CF_2O)_c$ $(CF_2O)_dCF_2CH_2OCH_2CH(OH)CH_2OH$ (Compound XIII) wherein c is 10.1, d is 10.9.

These compounds were checked for bonded ratio. Table 2 shows the results. It was confirmed that the present fluoropolyether compound I has effects of forming a lubricant layer which firmly adheres to the magnetic disk.

TABLE 2

| Specimen | Bonded ratio (%) |
|---|---|
| Compound I | 56 |
| Compound V (ADOH) | 56 |
| Compound XIII (Ztetraol-2000S) | 40 |

Example 5

Preparation of Magnetic Disk

Compounds I prepared in Example 1 was dissolved in Vertrel-XF, product of DuPont. The solution was 0.05 wt. % in the concentration of the compound. A magnetic disk, 2.5 inches in diameter, was immersed in the solution for 1 minute and then withdrawn at a rate of 2 mm/s. The disk was thereafter dried at 150° C. for 10 minutes. The coated compound was thereafter checked by FT-IR for film thickness.

Table 3 shows the results. It was confirmed that the magnetic disk can be obtained which is coated with the present compound having decomposition suppressing effects. Also a magnetic disk was prepared in the same manner by using Compound VII (A20H-DD).

TABLE 3

| Specimen | Film thickness (Å) |
|---|---|
| Compound I | 18 |
| Compound VII (A20H-DD) | 20 |

From the above, the perfluoropolyether compound of the present invention having a cyclophosphazene group and hydroxyl is satisfactory in both adhering properties and decomposition suppressing effects against $Al_2O_3$ in the component of the head, and it is confirmed that the magnetic disk can be obtained which is coated with the compound.

INDUSTRIAL APPLICABILITY

The present fluoropolyether compound having a cyclophosphazene group and hydroxyl is a lubricant which is excellent in decomposition resistance. Further, the magnetic disk using the present compound as a lubricant exhibits high durability to contact or sliding movement between the head and disk.

EXPLANATION OF THE SYMBOL

Indicated at 1 is a substrate; at 2, a recording layer; at 3, a protective layer; and at 4, a lubricant layer.

The invention claimed is:
1. A compound of the formula (1)

wherein A is a group of the formula (a) below, B is a group of the formula (b) or (c) or (d) below, p is 0, 1 or 2, q is a real number of 2 to 10, R is $C_{1-4}$ fluoroalkyl, Ar is unsubstituted or substituted aromatic group with $C_{1-30}$ alkyl or $C_{1-30}$ alkoxyl, Rf is $—CF_2CF_2O$ $(CF_2CF_2CF_2O)_xCF_2CF_2—$ or $—CF_2CF_2CF_2O$ $(CF_2CF_2CF_2CF_2O)_yCF_2CF_2CF_2—$, x and y are each a real number of 0 to 50

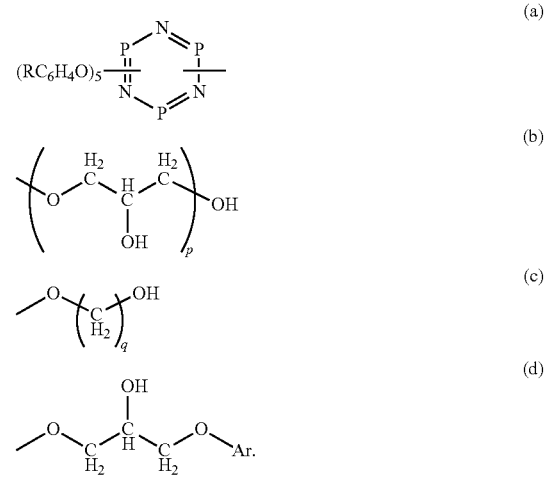

2. A compound as defined in claim 1 wherein B is a group of the formula (b), and p is 1 or 2.
3. A compound as defined in claim 1 wherein Rf is $—CF_2CF_2O(CF_2CF_2CF_2O)_xCF_2CF_2—$, x is a real number of 0 to 50.
4. A compound as defined in claim 1 wherein Rf is $—CF_2CF_2CF_2O(CF_2CF_2CF_2CF_2O)_yCF_2CF_2CF_2—$, y is a real number of 0 to 50.
5. A lubricant containing a compound of the formula (1)

wherein A is a group of the formula (a) below, B is a group of the formula (b) or (c) or (d) below, p is 0, 1 or 2, q is a real number of 2 to 10, R is $C_{1-4}$ fluoroalkyl, Ar is unsubstituted or substituted aromatic group with $C_{1-30}$ alkyl or $C_{1-30}$ alkoxyl, Rf is $—CF_2CF_2O$ $(CF_2CF_2CF_2O)_xCF_2CF_2$— or —$CF_2CF_2CF_2O(CF_2CF_2CF_2CF_2O)_yCF_2CF_2CF_2$—, x and y are each a real number of 0 to 50

(a)
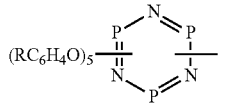

(b)
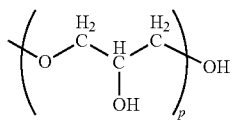

(c)
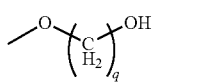

(d)
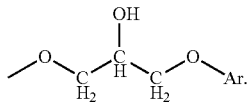

6. A lubricant as defined in claim 5 wherein B is a group of the formula (b), and p is 1 or 2.

7. A magnetic disk having at least a recording layer and a protective layer formed over a substrate, and a lubricant layer provided over a surface of the resulting assembly and comprising a compound containing a perfluoropolyether structure, the disk having a compound of the formula (1) as the lubricant layer A-O—$CH_2$—Rf—$CH_2$—B    (1)

wherein A is a group of the formula (a) below, B is a group of the formula (b) or (c) or (d) below, p is 0, 1 or 2, q is a real number of 2 to 10, R is $C_{1-4}$ fluoroalkyl, Ar is unsubstituted or substituted aromatic group with $C_{1-30}$ alkyl or $C_{1-30}$ alkoxyl, Rf is —$CF_2CF_2O(CF_2CF_2CF_2O)_xCF_2CF_2CF_2$— or —$CF_2CF_2CF_2O(CF_2CF_2CF_2CF_2O)_yCF_2CF_2CF_2$—, x and y are each a real number of 0 to 50

(a)
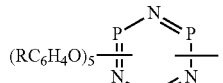

(b)
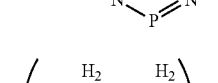

(c)
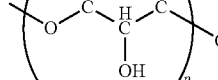

(d)
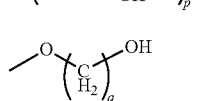

8. A magnetic disk as defined in claim 7 wherein B is a group of the formula (b), and p is 1 or 2.

* * * * *